(12) United States Patent
Braue, Jr. et al.

(10) Patent No.: US 6,472,437 B1
(45) Date of Patent: Oct. 29, 2002

(54) ACTIVE TOPICAL SKIN PROTECTANTS

(75) Inventors: Ernest H. Braue, Jr., Whiteford; Stephen T. Hobson, Belcamp; Erich K. Lehnert, Rosemont, all of MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 81 days.

(21) Appl. No.: 09/871,743

(22) Filed: Jun. 1, 2001

Related U.S. Application Data (60) Provisional application No. 60/209,337, filed on Jun. 2, 2000.

(51) Int. Cl.[7] .................... A61K 31/02; A61K 31/08; A61K 47/00; A61K 7/42
(52) U.S. Cl. .................. 514/759; 424/59; 514/723; 514/772; 514/789; 514/844; 514/845; 514/937; 514/939; 514/944
(58) Field of Search ...................... 424/89; 514/723, 514/759, 772, 789, 844, 845, 937, 939, 944

(56) References Cited

U.S. PATENT DOCUMENTS

| | | | |
|---|---|---|---|
| 4,649,037 A | 3/1987 | Marsh et al. | 423/338 |
| 5,607,979 A | 3/1997 | McCreery | 514/759 |
| 5,914,436 A | 6/1999 | Klabunde et al. | 588/205 |
| 5,990,373 A | 11/1999 | Klabunde | 588/200 |
| 6,057,488 A | 5/2000 | Koper et al. | 588/200 |
| 6,224,885 B1 | 5/2001 | Jenner | 424/401 |

OTHER PUBLICATIONS

Smith, et al., Jrnl. of the American Acad. of Dermatology, Vo. 32, No. 5, part 1, May 1995, pp. 765–776, Sulfur mustard: Its continuing threat as a chemical warfare agent, the cutaneous lesions induced, progress in understanding its mechanism of action, its long–term health effectgs, and new developments for protection and therapy.

Arroyo, et al., Jrnl. of Pharm. and Toxicol. Methods, vol. 33, No. 2, Apr. 1995, pp. 109–112, EPR/Spin–Label Technique as an Analystical Tool for Determining the Resistance of Reactive Topical Skin Protectants (rTSPs) to the Breakthrough of Vesicant Agents.

*Primary Examiner*—Shelley A. Dodson
(74) *Attorney, Agent, or Firm*—Elizabeth Arwine (57) ABSTRACT

A topical skin protectant formulation containing a barrier cream and an active moiety for protecting warfighters and civilians against all types of harmful chemicals, specifically chemical warfare agents (CWAs). The topical skin protectant offers a barrier property and an active moiety that serves to neutralize chemical warfare agents into less toxic agents.

19 Claims, 4 Drawing Sheets

Figure 1. Decision Tree Network used to evaluate active TSPs.

Figure 2. Structures of compounds incorporated into active TSPs

Figure 3. ¹H NMR Spectra of CEES and reaction products with IBDA

Figure 4. IBDA + Y25 before and after addition of CEES.

ACTIVE TOPICAL SKIN PROTECTANTS

PRIORITY INFORMATION

This applications claims the benefit of priority of U.S. Provisional Application No. 60/209,337 filed Jun. 2, 2000.

BACKGROUND OF THE INVENTION

1. Field of the Invention

This invention relates to active topical skin protectants. More specifically, the invention relates to an active barrier cream for protection against all types of harmful chemicals, specifically chemical warfare agents (CWAs). The active barrier cream is applied prior to exposure on the skin of persons at risk of exposure to harmful chemicals to provide a protective barrier for the skin. The active barrier cream chemically or physically reacts with harmful chemicals such as CWAs (vesicants and nerve agents) to neutralize these harmful chemicals while the barrier properties of the cream prevent penetration of harmful chemicals through the cream to the skin.

2. Description of Related Art

The concept of applying a topical protectant to vulnerable skin surfaces before entry into a chemical combat arena has been proposed as a protective measure against percutaneous CWA toxicity since the first use of CWAs in World War I. The protectant was applied to vulnerable skin surfaces prior to entry into a chemical combat area. Topical protectants should augment the protection afforded by the protective overgarments and/or redefine the circumstances requiring mission oriented protective posture (MOPP) levels. The rapid action of vesicating agents, also known as blistering agents, such as sulfur mustard (HD) and lewisite (L), require a pre-exposure skin protection system or a contamination avoidance approach that may preclude the percutaneous toxicity of these agents. These approaches also reduce the risk of exposure to organophosphorus (OP) chemical agents (nerve agents), which unlike the vesicating agents, are lethal in droplet amounts.

An organic molecule, S-330, that reacts with CWAs was incorporated in a product and fielded as the M-5 ointment kit at the end of World War II (Formula 1)

Formula 1

S-330

S-330

However, the unacceptable barrier properties and the undesirable cosmetic properties (specifically foul odor and sticky texture) caused a recall of this product.

Two non-active topical skin protectant (TSP) formulations were developed at the United States Army Medical Research Institute of Chemical Defense (USAMRICD) and were transferred to advanced development following a Milestone Zero (MS0) Review in October 1990. The timeline of the approval of the TSP continued with MSI in 1993, an Investigational New Drug (IND) filed with the FDA in 1994, MSII in 1995, and culminated with New Drug Application (NDA) approval in February, 2000. Upon approval by the FDA, the TSP was designated Skin Exposure Reduction Paste Against Chemical Warfare Agents (SERPACWA). SERPACWA is a 50:50 (wt/wt) mixture of perfluoropolyether oil (Fomblin® Y25 from Ausimont) and poly (tetrafluoroethylene) (polymist® F5a powder from Ausimont). The formulation described in McCreery U.S. Pat. No. 5,607,979 is directed to a topical skin protectant cream that acts as a barrier to CWAs.

Although SERPACWA extends the protection afforded by MOPP and allows a longer window for decontamination, it does not completely remove the possibility for contamination because the CWA is not neutralized. To avoid contamination of other areas of the battlefield and to preclude the future percutaneous absorption of the CWA, decontamination is still required. Furthermore, although the McCreery formulation provides excellent protection against GD and HD liquid, its protection against HD vapor is minimal.

To overcome these deficiencies, there is a need for a new TSP that contains an active component. This active Topical Skin Protectant (active TSP) was developed within the following criteria. First, the active TSP should neutralize CWAs including but not limited to sulfur mustard (HD), soman (GD), and VX. Second, the barrier properties of the TSP should be maintained or increased. Third, the protection against HD vapor should increase. And fourth, the cosmetic characteristics (i. e. odor, texture) of the TSP should be maintained.

This invention meets the above criteria and solves the problems associated with the past TSPs by providing an active topical skin protectant that increases effectiveness of the TSP barrier quality and neutralizes CWAs into less harmful products.

It is therefore, an objective of the present invention to provide an active topical skin protectant that prevents the percutaneous absorption of CWAs and converts these toxic materials into less harmful products.

It is a further objective of the present invention to provide an active topical skin protectant that maintains desirable cosmetic properties making it acceptable to the user. Specifically, the active TSP should not be sticky, should be without offensive odor, and should be nonirritating to the skin.

It is still a further object of the invention to provide an active topical skin protectant that is practical for field operations. Specifically, the active TSP should have a stable shelf life, not be easily washed off with water, and should not react with insecticides or camouflage paint.

SUMMARY OF THE INVENTION

A topical skin protectant formulation for neutralizing chemical warfare agents into less toxic products comprising: a barrier base cream and one or more active moieties. The base cream comprises poly(tetrafluoroethylene) resins dispersed in perfluorinated polyether oils. The active moieties that have been found to be effective with the base cream are listed in Table 1. The active barrier cream is applied to the skin prior to exposure of persons at risk of exposure to harmful chemicals to provide an active barrier to protect the skin. The active barrier cream chemically or physically reacts with harmful chemicals such as CWAs to neutralize these harmful chemicals while the barrier properties of the cream prevent penetration of harmful chemicals through the cream to the skin.

DETAILED DESCRIPTION

Candidate Active Moieties

The types of materials that neutralize harmful agents use three main modes of action: oxidation, reduction or hydrolysis.

The selection of the active materials, however, is restricted by operating criteria. Thus, the active moiety must not irritate the skin, react with insecticides or camouflage paints or be unstable. This restriction eliminates many of the most active species. Futhermore, the active moiety must be incorporated into a highly fluorinated environment that is not amenable to many reaction pathways.

Tables 1–3 are a list of active moieties that are acceptable for use in the present invention:

TABLE 1

LIST OF ACTIVE COMPOUNDS AND EXAMPLE FORMULATIONS FOR ACTIVE TOPICAL SKIN PROTECTANTS

| ICD # | Active Moiety | CAS # | % Active | % other | % PFPE | % PTFE |
|---|---|---|---|---|---|---|
| 2885 | Iodobenzene Diacetate | 3240-34-4 | 10 | light surfactant (2853) 10 | 40 | 40 |
| 2902 | Iodobenzene Diacetate | 3240-34-4 | 10 | (3004) 80 light surfactant (2853) 10 | | |
| 3056 | High Test Hypochlorite, Ca(OCl)$_2$ | 7778-54-3 | 10 | (1511) 90 | | |
| 3057 | High Test Hypochlorite, Ca(OCl)$_2$ | 7778-54-3 | 10 | light surfactant (2853) 10 Water 10 | 50 | 20 |
| 3058 | High Test Hypochlorite, Ca(OCl)$_2$ | 7778-54-3 | 10 | light surfactant (2853) 10 Water 10 | 50 | 20 |
| 3059 | Chloramine T | 127-65-1 | 10 | (1511) 90 | | |
| 3060 | Chloramine B | 127-52-6 | 10 | (1511) 90 | | |
| 3315 | Iodobenzene diacetate | 3240-34-4 | 10 | light surfactant (2853) 10, (3004) 80 | | |
| 3366 | Iodobenzene diacetate | 3240-34-4 | 8 | light surfactant (2853) 8 | 42 | 42 |
| 3321 | Activated Carbon | 7440-44-0 | 10 | | 53.8 | 37.5 |

TABLE 2

LIST OF ACTIVE COMPOUNDS AND EXAMPLE FORMULATIONS FOR ACTIVE TOPICAL SKIN PROTECTANTS

| ICD # | Active Moiety | % Active | % other | % PFPE | % PTFE |
|---|---|---|---|---|---|
| 3150 | XE555 resin | 10 | H$_2$O 10 (2853) 10 | 40 | 30 |
| 3151 | XE555 resin | 7.5 | | 62.5 | 30 |
| 3311 | XE555 resin | 5.6 | | 94.4 | |

TABLE 3

LIST OF ACTIVE COMPOUNDS AND EXAMPLE FORMULATIONS FOR ACTIVE TOPICAL SKIN PROTECTANTS

| ICD # | Active Moiety | % Active | % other | % PFPE | % PTFE |
|---|---|---|---|---|---|
| 3488 | Potassium O,O'-Dioctanylphosphorodithioate | 5 | | 49 | 46 |
| 3587 | Potassium O,O'-Dibutanylphosphorodithioate | 10 | | 45 | 45 |

TABLE 3-continued

Abbreviations for Tables 1–3:

| | |
|---|---|
| PTFE: | poly(tetrafluoroethylene) available as F5A powder from Ausimont, Morristown, NJ |
| PFPE: | perfluoropolyether available as FOMBLIM ™ Y25 oil from Ausimont, Morristown, NJ |
| ICD2853 | Krytox ® light PFPE Surfactant, Dupont, Wilmington, DE (CAS #60162-51-4) |
| ICD3004 | SERPACWA, Skin Exposure Reduction Past Against Chemical Warfare Agents, 50% PTFE, 50% PFPE |
| ICD2289 | same formulation as composition as SERPACWA and ICD3004 |
| ICD1511 | 30% PTFE (L-206 powder from Ausimont) and 70% YR PFPE (as FOMBLIM ™ YR oil from Ausimont) |
| XE555 resin | Available as Ambergard XE-555 ® from Rohm and Haas, Philadelphia, PA |
| CAS # | Chemical Abstract Service Registry Numbers |

Percentages are in weight percents
*A light surfactant is a low molecular weight oil.

The percent values assigned to the above listed components of the example skin protectant formulations are given for example only. These values may be adjusted up or down and still embody the spirit of the invention if the herein described qualities of efficacy and composition of the present invention are met.

Figure 2:
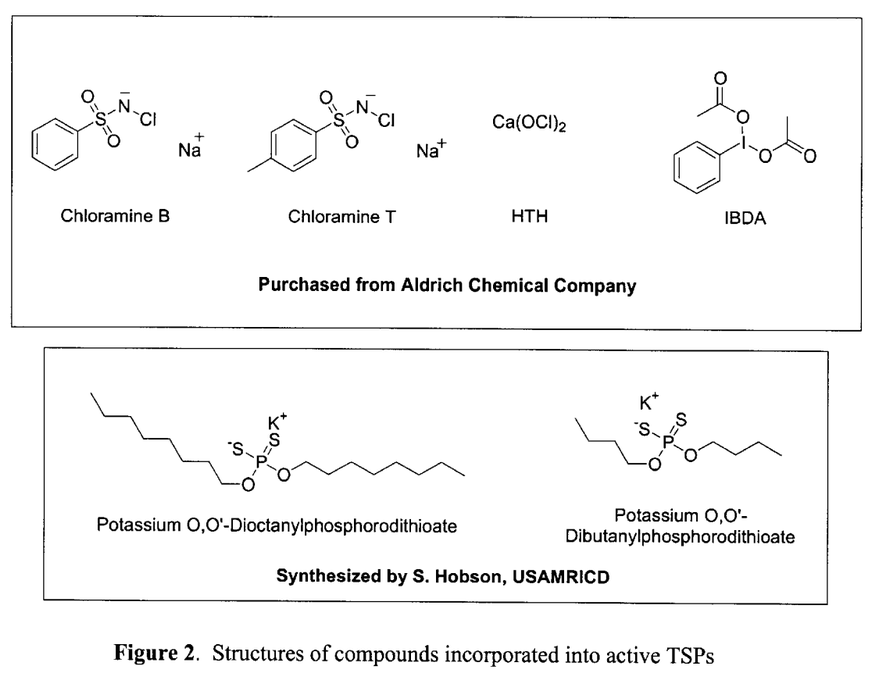
FIG. 2 is the structure of organic and inorganic molecules incorporated into the active TSP.

All active moieties listed above are useful for both liquid and vapor challenges. The amount of each varies with each formulation. The object is to optimize the quantity of active moiety in the base cream without loosing the barrier properties of the base cream. The amount of active moiety can vary from about 1–30%. The amount of perfluorinated polyether oil can vary from about 40 to 60%. The amount of poly(tetrafluoroethylene) can vary from about 30 to 50%. All compounds except for the XE-555 resin are small organic or inorganic molecules (FIG. 2).

The XE-555 resin is a commercial compound currently used in the U.S. Army M-291 Chemical Decontamination kit.

One criterion for selection of the active materials is increased efficacy against HD and/or GD vapor. The best candidate compound listed in Table 1 for HD is ICD2902 and for GD is ICD3056.

All compounds must also be incorporated into the TSP matrix without degradation of the barrier properties. These materials were incorporated into the cream either as solids or aqueous suspensions. Typically they are dispersed into the perfluorinated oil followed by sequential addition of the appropriate amount of F5A PTFE.

SERPACWA (ICD3004) consists of fine particles of poly(tetrafluoroethylene) resin dispersed in perfluorinated polyether oil. The excellent barrier properties of this high molecular weight polymer formulation are related to the low solubility of most materials in it. Only highly fluorinated solvents like Freon® have been observed to show appreciable solubility. This aprotic non-polar polymer mixture provides a unique medium for active moieties of the invention. Reaction mechanisms that do not involve charged transition states should be favored in this chemical environment.

Base creams formed from about 35–50% fine particulates of certain poly(tetrafluoroethylene) PTFE resins dispersed in perfluorinated polyether oils (PFPE) having viscosities from about 20 cSt to about 500 cSt afford good protection against chemical warfare agents such as HD, L, sulfur mustard/Lewisite mixtures (HL), pinacolyl methylphosphonofluoridate (soman or GD), thickened soman (TGD) and O-ethyl S-(2-diisopropylaminoethyl)methylphosphonothiolate (VX). PTFE and PFPE are available commercially from Ausimont (Morristown, N.J.) and Dupont (Wilmington, Del.).

The base creams used in the invention are suspensions of 35–50% finely divided PTFE having a surface area below about 6 $m^2/g$ in a perfluorinated polyether base oil prepared from poly(perfluoropropylene oxide), which has a viscosity between about 20 and about 500 cSt. More preferred compositions comprise from about 35% to about 50% of finely divided PTFE having an average particle size from about 0.1 $\mu$m to about 10 $\mu$m and a surface area below about 4 $m^2/g$ in a perfluorinated polyether base oil from 40% to 60% having a viscosity between about 20 and about 500 cSt.

Suitable perfluorinated polyether oils are Fomblin® HC- and Y-oils (Ausmont) and Krytox.® oils (Dupont). The Fomblin® oils are mixtures of linear polymers based on poly(perfluoropropylene oxide) having the following chain structure: $CF_3\text{-}[(OCF(CF_3)CF_2)_n\text{—}(OCF_2)_m]OCF_3$. The Krytox® oils are mixtures of linear polymers also based on poly(perfluoropropylene oxide) and have the chemical structure $F\text{—}[(CF(CF_3)CF_2O)]_m CF_2CF_3$. Fomblin® Z oils having the formula: $CF_3\text{-}[(OCF_2CF_2)_n\text{—}(OCF_2)_m]\text{—}OCF_3$, may also be useful in the practice of the invention. The indices n and m indicate the average number of repeating polymeric subunits in the oil molecules. The oils may have a viscosity of about 20 cSt to about 500 cSt or more. The creams were generally prepared according to U.S. Pat. No. 5,607,979, incorporated herein in its entirety.

Other additives to the base cream are water and surfactants (see Tables 1–3). The surfactant facilitates the mixing of the water with the base cream. An example of a typical surfactant is perfluoropolyalkylether (Krytox® CAS #60164-51-4 from Dupont). Additional materials may also be incorporated as long as they do not reduce effectiveness of the topical protectant, such as stabilizers, camouflage paints, and sunscreens.

A further understanding of the composition of the topical protectant of the invention can be obtained by reference to certain specific example formulations set forth in Tables 1–3. These examples are provided herein for purposes of illustration only and are not intended to be limiting. Many active moieties require the presence of water as a reagent for the hydrolysis of HD and GD. The active moieties that react by a hydrolysis mechanism require the presence of water. When the topical protectant is applied to the skin of a user, moisture in the form of perspiration may also aid in the hydrolysis of HD and GD. The addition of perfluorinated polyether surfactants to the base cream facilitates the addition of water.

Temperature and mixing sheer should be monitored to maintain the base cream at the desired consistency and quality. The active TSPs are typically prepared at ambient temperature using mechanical mixing. Depending on the oxygen sensitivity of the active material, some of the active materials may be added to the perfluorinated oil under an inert (i.e. nitrogen) atmosphere. Mixing times of 10–20 are usually sufficient for dispersal of solids into the SERPACWA matrix. A typical procedure for the preparation of an active aTSP with the XE-555 resin is presented below:

In a polypropylene container is added the appropriate amount of resin (5–10%) by weight, Y25 (50–55% by weight) perfluorinated oil, and any additive. The suspension is mixed with a mechanical stirrer at ambient temperature for 5 to 15 minutes. To the suspension is added F5A poly(tetrafluoroethylene) in three portions with vigorous mechanical stirring for 5 to 10 minutes between each addition. After final addition the container is tightly capped and sealed with Parafilm®.

Multilayer Approach

Although an active TSP can be generally the application of a powder that is a POM/RNP sprinkled on the skin, or an active moiety in a base cream wherein the cream is spread on the skin, a multilayering approach can also be used. The multilayer approach would be to use the active TSP as the first layer and a solid active moiety powder as the second layer. The second layer would be a thin coating of the solid active moiety powder sprinkled over the active TSP cream. This approach would provide a concentrated decontamination material at the surface of the barrier cream, which would accelerate the neutralization process of CWAs coming in contact with the surface. Alternatively, the first layer can be a thin coating of the solid active moiety powder followed by a second layer of the active TSP.

Testing

Figure 1:
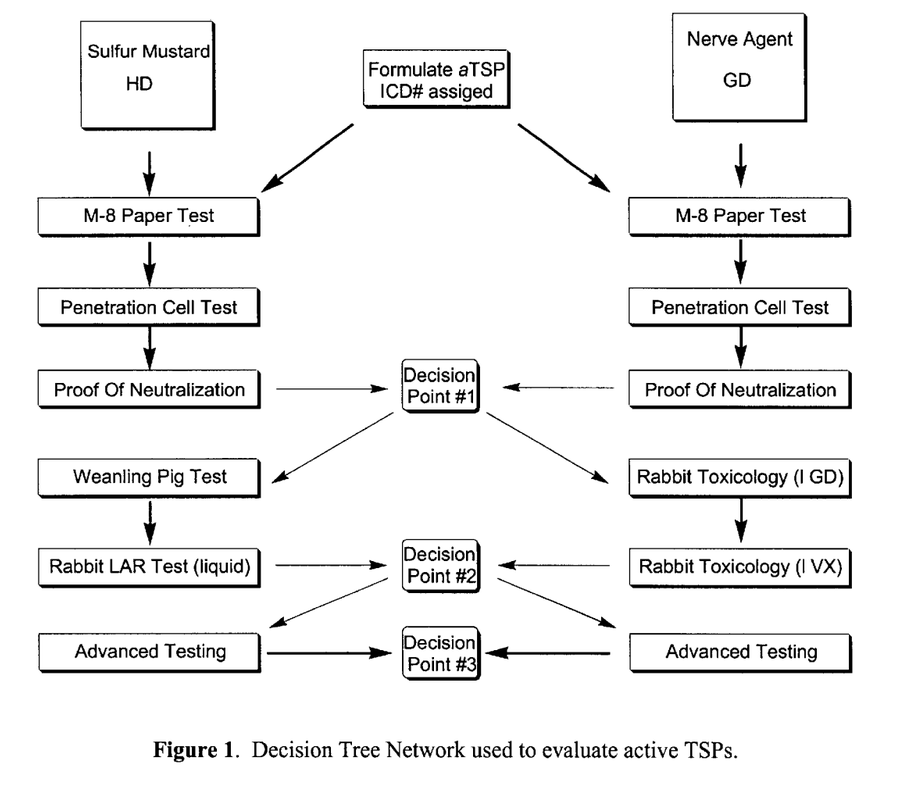
FIG. 1 is a flow diagram of the active TSP Decision Tree Network for efficacy evaluation.

Evaluation of formulations was conducted with a decision tree network (DTN) that describes the path that active TSPs follow during evaluation (FIG. 1).

The DTN is divided into two pathways: one for vesicants and the other for nerve agents. Within these pathways there are three blocks each with a decision point. The first block consists of a series of three mechanical (in vitro) modules used to determine the initial efficacy of candidate formulations and to eliminate non-effective candidates before animal testing, the second block consists of in vivo modules and the third block consists of an advanced animal module to determine the influence of time, water and interactions with other products.

The M8 paper test is used to evaluate the barrier resistance of liquid CWA challenges, including HD, pinacolyl methylphosphonofluoridate (soman, GD), and O-ethyl S-(2-diisopropylaminoethyl)methylphosphonothioate (VX). In this test a 0.15 mm layer of active TSP is placed over a well-defined area of M8 chemical detection paper and challenged with an 8 $\mu$l droplet of CWA. When agent penetrates the active TSP barrier and reaches the M8 paper, a colored spot develops on the paper. The test assemblies are observed for 6 hr and the breakthrough time is reported for each sample. A total of nine replicates are run for each test, and a standard reference compound is included each day for quality control.

The penetration cell test is used to evaluate the barrier properties against both liquid and vapor CWA challenges (Braue, E. H. Jr. *Journal of Applied Toxicology*, 1999, 19(S), S47–S53). In this test the lower half of a Reifenrath diffusion cell (Reifenrath Consulting and Research, Richmond, Calif.) is used. A 0.15 mm thick layer of active TSP is supported by nitrocellulose paper on top of the cell. The active TSP layer is challenged with a 10 $\mu$l liquid droplet of HD or an 8 $\mu$l droplet of GD, or a saturated vapor cup of HD or GD. Breakthrough of CWA into the lower chamber of the diffusion cell is monitored using a miniature continuous air monitoring system (MINICAMS, CMS Research, Birmingham, Ala.). This system has been automated to allow continuous monitoring of five cells in a 40-min cycle. The test runs for 20 hr and the accumulated amounts of agent that break through the active TSP barrier are calculated. From these data, we obtained two values: the cumulative amount of CWA that penetrates through the active TSP, and the time at which a "breakthrough" occurs. We defined "breakthrough" values at the minimum amount of HD (1000 ng) and GD (1000 ng) that results in a physiological response. Minimal amount of HD for vesication=1000 ng. See F. R. Sidell, J. S. Urbanetti, W. J. Smith, and C. G. Hurst in *Textbook of Military Medicine, Medical Aspects of Chemical and Biological Warfare*, edited by F. R. Sidell, E. T. Takafuji, and D. R. Franz (Office of the Surgeon General at TMM Publications, Washington, D.C. 1997) p 201. $LD_{50}$ for soman (GD)=350 mg/70 kg man. See F. R. Sidell in *Textbook of Military Medicine, Medical Aspects of Chemical and Biological Warfare*, edited by F. R. Sidell, E. T. Takafuji, and D. R. Franz (Office of the Surgeon General at TMM Publications, Washington, D.C. 1997) p 141. These two values allow us to rank the active TSP formulations and to select the appropriate component for advanced development.

The proof-of-neutralization test is used to verify that active TSP formulations actually neutralize CWAs into less toxic materials. This test uses the headspace solid phase microextraction (HS-SPME) technique for the collection of CWAs. Samples collected on the extraction filament are analyzed by gas chromatography/mass spectroscopy. 100 mg of active TSP formulation are challenged with 0.1 $\mu$l of neat CWA (HD, GD, or VX) in a small vial. The headspace above the mixture is sampled periodically to determine the amount of CWA remaining in the flask. Efficacy is determined by the % loss of CWA. Other analytical techniques such as Nuclear Magnetic Resonance (NMR) and Fourier-Transform Infrared Spectrometry (FTIR) have also been used in this module.

Formulations that pass this initial set of screens are moved into the second phase of testing using animal models. The weanling pig test for HD vapor evaluates a 0.10 to 0.20 mm thick layer of active TSP spread on the depilated dorsa. The standard saturated vapor cup is used for a 15–60 min challenge. The effectiveness of the active TSP is determined by measuring the degree of erythema that developed on the skin exposure site. Erythema is measured objectively using a reflectance calorimeter (see Braue, E. H. Jr. *Journal of Applied Toxicology*, 1999, 19(S), S47–S53)

The rabbit lesion area ratio (LAR) test is used to evaluate a challenge by HD liquid. In this test, a 0.10 mm layer of active TSP spread on the clipped dorsa is challenged with 1.0 $\mu$l of liquid HD. The effectiveness of the active TSP is determined by measuring the lesion areas of protected and non-protected sites.

The rabbit acetyl cholinesterase (AChE) inhibition test is performed by applying a 0.10mm thick layer of active TSP on the clipped dorsa of rabbit followed by a fixed dose of GD (1 $LD_{50}$), TGD (1 $LD_{50}$), or VX (20 $LD_{50}$). The effectiveness of the active TSP is determined by lethality and also by measuring the erythrocyte acetyl cholinesterase activity 0.5, 1, 2, and 24 hr following exposure.

Candidate formulations that pass the in vivo test modules move into advanced animal testing. These tests are similar to the initial animal tests with the addition of stresses for wear-time and washing with water. Interactions with other products that a soldier might use are also evaluated. These products include camouflage paints, sunscreens and insecticides.

Results

Due to the variety of compounds investigated, multiple neutralization reactions are possible. For example, iodobenzene diacetate, reacts to neutralize sulfur mustard via oxidation (Scheme 1)

Scheme 1. Possible neutralization reactions of IBDA with HD.

In contrast, the phosphorodithioate react via substitution followed by hydrolysis (Jaeger, D. A. Schilling, C. L. III, Zelenin, B. L.; Kubicz-Loring, E. *Langmuir* 1999,15, 7180) (Scheme 2).

Scheme 2. Possible neutralization reaction of phosphorodithioates with HD.

Finally, one would expect that the major mode of action for the XE-555 resin to be either physical adsorption or acid catalyzed dehydrohalogenation (Scheme 3)

Scheme 3. Possible neutralization reactions of XE-555 Resin with HD

Against GD vapor, the most effective moieties were the active chlorine compound. In this case, it is likely that the inorganic or organic compound is assisting in the hydrolysis of GD (Scheme 4).

Scheme 4. Hydrolyses of soman (GD) with HTH active TSP.

Since the XE-555 resin has a high surface area, the GD may also be physically adsorbed.

The efficacy of inorganic or organic compounds in active TSPs against GD vapor were monitored by the penetration time of 1000 ng of GD vapor compared to SERPACWA (ICD 3004) (Chart 1).

Chart 1

Time for 1000 ng GD to penetrate aTSPs with inorganic or organic compounds.

The cumulative amount of GD vapor that penetrates the active TSP over 20 hours also demonstrates the efficacy of inorganic or organic compounds in active TSPs (Chart 2).

GD (v) Pentration Cell

Chart 2

Cumulative amount of GD vapor through aTSP over 20 hr.

Formulation ICD 3056 shows the greatest protection against GD vapor reducing the amount of GD by 96%. The only other formulations displaying significantly (P=0.05) increased protection in the penetration cell model against GD compared to SERPACWA (ICD 3004) is ICD 3057.

The increase in protection for the inorganic or organic compounds was first measured for ICD 2885 and 2902 in the M8 paper test. Upon exposure to liquid HD, both compounds display no breakthroughs. This protection was also demonstrated in the increase in the time needed for 1000 ng of HD vapor to penetrate the active TSP as compared to SERPACWA (ICD 3004) as measured in the penetration cell model (Chart 3).

HD (v) Pentration Cell

Chart 3

Time for 1000 ng HD to penetrate active TSPs listed in Tables 1, 2, and 3.

A comparison of the cumulative amount of HD vapor that penetrates the active TSP over 20 hours also shows the increase in protection (Chart 4).

HD (v) Pentration Cell

[Bar chart: Cumulative amount at 20 hr (ng, SD) vs ICD Number — 3150, 3004, 3488, 3151, 3151, 2902, 2902]

Chart 4

Cumulative amount of HD vapor through aTSP over 20hr. As clearly seen in Chart 4, active TSPs with either IBDA (2902) or XE-555 resin show outstand protection against HD in the penetration cell mode. In fact, as few as 4 ng of HD vapor (ICD 2902) was detected in the penetration cell module.

In addition to the penetration cell model, certain active TSP containing inorganic or organic compounds were tested in the head space solid phase micro-extraction gas chromatography/mass spectrometry (HS-SPME/GC-MS) test against HD. (Chart 5).

Head Space Solid Phase Microextraction Gas Chromatography/Mass Spectrometry (HS-SPME-GC/MS)

[Bar chart: Time to 1000 ng (min, SD) vs ICD Number — 3311, 3366, 3315, 3151, 3004]

Chart 5

Evaluation of active TSPs containing inorganic or organic compounds against HD liquid using HS-SPME-GC/MS.
In this module significant efficacy was seen against HD in all active TSPs tested.

Figure 3:
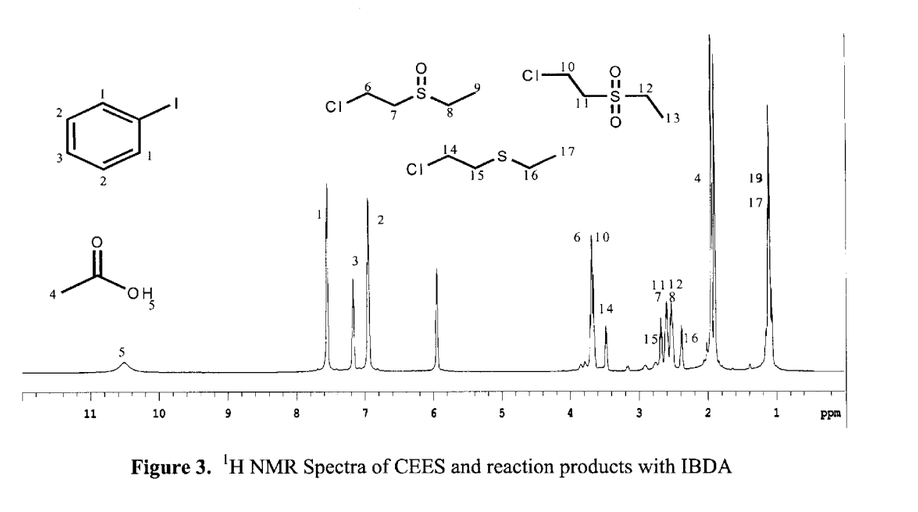
FIG. 3 is the $^1$H NMR Spectra of CEES and reaction products with IBDA.

Possible neutralization pathways of these organic compounds were probed using NMR with CEES as an HD simulant. In these experiments, IBDA (ICD 2902) was suspended in Y25 oil (2.5% by weight), the simulant (CEES) was added, and the suspension was stirred under ambient conditions for 12 to 24 hours. NMR spectra were then obtained using gradient multi-quantum coherence spectrometry (g-HMQC) and 1H NMR to monitor the neutralization of CEES (FIG. 3).

Figure 4:
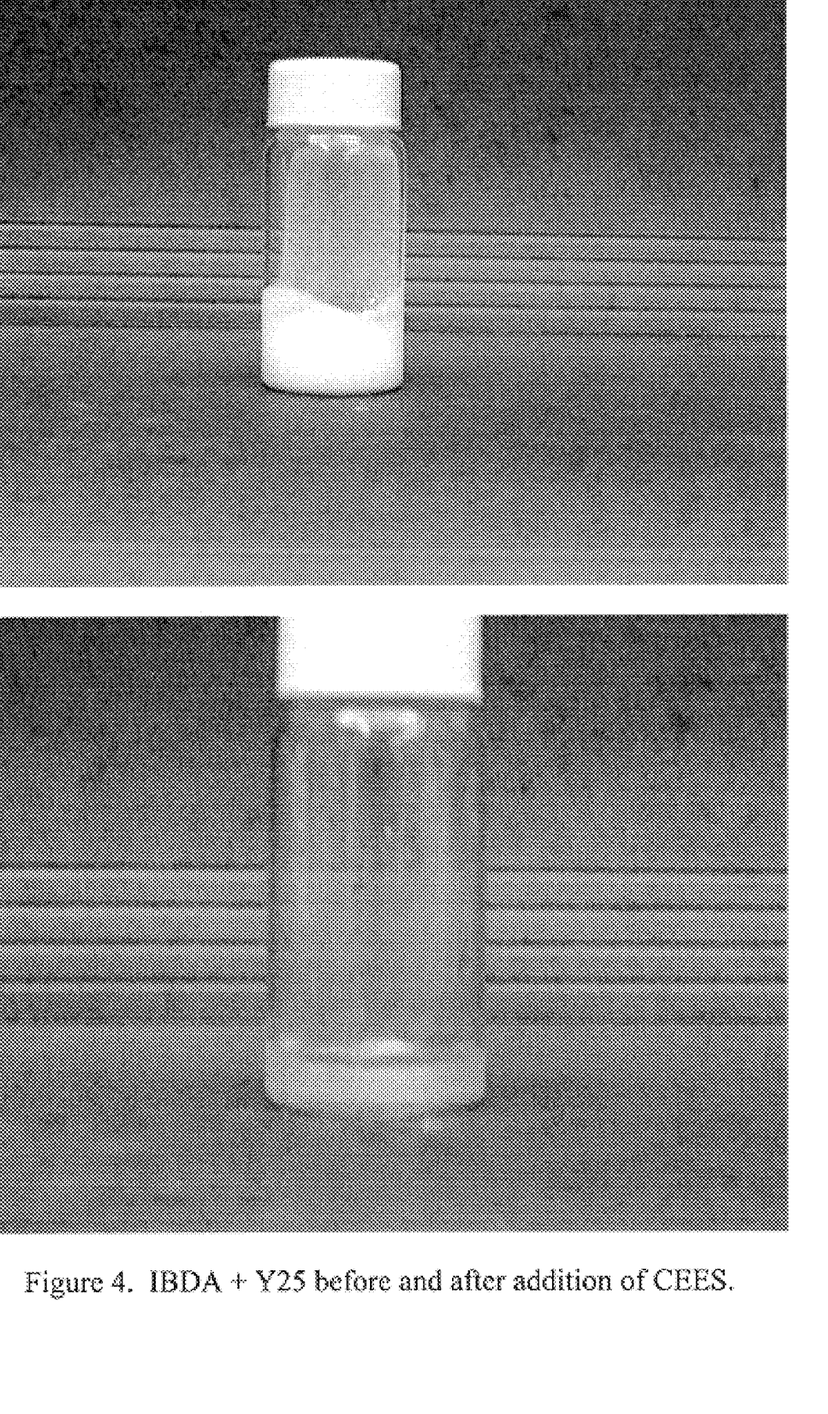
FIG. 4 is a photograph of IBDA+Y25 before and after addition of CEES.

Thus, IBDA reacts with CEES to give not only the non-toxic sulfoxide, but also the toxic sulfone. This reaction is also evident by visual examination of the IBDA suspension before (top, FIG. 4) and 24 hours after addition of CEES (bottom, FIG. 4).

The performance of the active TSPs containing IBDA or XE-555 Resin in the penetration cell was reflected the weanling pig model at short exposure times (Chart 6).

Chart 6

Results of active TSPs containin XE555 resin (ICD 3151) and IBDA (ICD 2902). Controls are all 15min exposures with no TSP Since the active TSPs containing IBDA reduced the cumulative amount of HD vapor in the penetration cell by between 90 and 99% (Chart 4), it satisfying to see the results reflected in the recorded erythema from HD vapor with a 15-minute exposure time. However, when the exposure time is increased, the observed protection is degraded. Thus, at 30 minutes only the IBDA formulation has significant protection, and at 45 and 60 minutes, no protection is offered. These data may be due to saturation of the XE-555 resin or the IBDA in the active TSP. Furthermore, this is not unexpected because neither compound is catalytic (see Scheme 2, 3). On the other hand, it is possible that the neutralization products (i.e., HD sulfone) may be causing the increase in erythema.

Having now fully described the invention, it will be apparent to one of ordinary skill in the art that many changes and modifications can be made thereto without departing from the spirit or scope of the invention as set forth herein thereto without departing from the spirit or scope of the invention as set forth herein

What is claimed is:

1. A topical skin protectant formulation for neutralizing chemical warfare agents into less toxic products comprising: a barrier base cream; and one or more Iodobenzene Diacetate; High Test Hypochlorite; Chloramine T; Chloramine B; active carbon; XE555 resin; Potassium O,O'-Dibutanylphosphorodithioate; and Potassium O,O'-Dibutanylphosphorodithioate as an active moiety.

2. The topical skin protectant formulation of claim 1, wherein the base cream comprises poly(tetrafluoroethylene) resins dispersed in perfluorinated polyether oils.

3. A topical skin protectant formulation for neutralizing chemical warfare agents into less toxic products comprising:
   (a) a barrier base cream, said barrier base cream comprising poly(tetrafluoroethylene) resins dispersed in perfluorinated polyether oils; and
   (b) one or more active moieties selected from the group consisting of: Iodobenzene Diacetate; High Test Hypochlorite; Chloramine T; Chloramine B; active carbon; XE555 resin; and Potassium O,O'-Dibutanylphosphorodithioate; and Potassium O,O'-Dioctanylphosphorodithioate.

4. The topical skin protectant formulation of claim 3, further comprising one or more additives.

5. The topical skin protectant formulation of claim 4, wherein said additives comprise one or more of water, surfactant, stabilizers, camouflage paints, and sunscreens.

6. A topical skin protectant formulation for neutralizing chemical warfare agents into less toxic products comprising:
   (a) a barrier base cream, said barrier base cream comprising poly(tetrafluoroethylene) resins dispersed in perfluorinated polyether oils;

(b) one or more active moieties selected from the group consisting of: Iodobenzene Diacetate; High Test Hypochlorite; Chloramine T; Chloramine B; active carbon; XE555 resin; and Potassium O,O'-Dibutanylphosphorodithioate; and Potassium O,O'-Dioctanylphosphorodithioate; and (c) one or more additives.

7. The topical skin protectant formulation of claim 6, wherein said additives comprise one or more of water, surfactant, stabilizers, camouflage paints, and sunscreens.

8. A topical skin protectant system comprising:

a) a topical skin protectant formulation for neutralizing chemical warfare agents into less toxic products comprising a barrier cream and one or more active moieties, said active moieties selected from the group consisting of: Iodobenzene Diacetate; High Test Hypochlorite; Chloramine T; Chloramine B; active carbon; XE555 resin; and Potassium O,O'-Dibutanylphosphorodithioate; and Potassium O,O'-Dioctanylphosphorodithioate; and b) a second formulation for applying a thin solid active moiety powder on top or below said topical skin protectant formulation comprising one or more active moieties selected from the group consisting of: Iodobenzene Diacetate; High Test Hypochlorite; Chloramine T; Chloramine B; active carbon; XE555 resin; and Potassium O,O'-Dibutanylphosphorodithioate; and Potassium O,O'-Dioctanylphosphorodithioate.

9. A method of protecting a user against chemical warfare agents comprising: applying a topical skin protectant formulation for neutralizing chemical warfare agents into less toxic products comprising:

a) a barrier cream; and b) one or more active moieties, said one or more active moieties selected from the group consisting of: Iodobenzene Diacetate; High Test Hypochlorite; Chloramine T; Chloramine B; active carbon; XE555 resin; Potassium O,O'-Dibutanylphosphorodithioate; and Potassium O,O'-Dioctanylphosphorodithioate.

10. A method of protecting a user against chemical warfare agents comprising:

a) applying a first thin layer of a solid active moiety powder, said solid active moiety powder selected from the group consisting of: Iodobenzene Diacetate; High Test Hypochlorite; Chloramine T; Chloramine B; active carbon; XE555 resin; and Potassium O,O'-Dioctanylphosphorodithioate; and b) applying a second layer of a topical skin protectant formulation for neutralizing chemical warfare agents into less toxic products comprising a barrier cream and one or more active moieties, said one or more active moieties selected from the group consisting of: Iodobenzene Diacetate; High Test Hypochlorite; Chloramine T; Chloramine B; active carbon; XE555 resin; Potassium O,O'-Dibutanylphosphorodithioate; and Potassium O,O'-Dioctanylphosphorodithioate.

11. A method of protecting a user against chemical warfare agents comprising:

a) applying a first layer of a topical skin protectant formulation for neutralizing chemical warfare agents into less toxic products comprising a barrier cream and one or more active moieties, said one or more active moieties selected from the group consisting of: Iodobenzene Diacetate; High Test Hypochlorite; Chloramine T; Chloramine B; active carbon; XE555 resin; and Potassium O,O'-Dioctanylphosphorodithioate; and b) applying a thin layer of solid active moiety powder over the first layer, said solid active moiety powder selected from the group consisting of: Iodobenzene Diacetate; High Test Hypochlorite; Chloramine T; Chloramine B; active carbon; XE555 resin; Potassium O,O'-Dibutanylphosphorodithioate; and Potassium O,O'-Dioctanylphosphorodithioate.

12. A method of making a topical skin protectant formulation comprising: mixing a) one or more active moieties, said one or more active moieties selected from the group consisting of: Iodobenzene Diacetate; High Test Hypochlorite; Chloramine T; Chloramine B; active carbon; XE555 resin; Potassium O,O'-Dibutanylphosphorodithioate; and Potassium O,O'-Dioctanylphosphorodithioate; with b) a barrier cream comprising poly(tetrafluoroethylene) resins dispersed in perfluorinated polyether oils.

13. A topical skin protectant formulation comprising a formulation selected from the group consisting of:

(a) about 10% Iodobenzene Diacetate, about 40% pefluoropolyether oil, about 40% poly(tetrafluoroethylene), and about 10% light surfactant;

(b) about 10% Iodobenzene Diacetate, about 10% of a 50% poly(tetrafluoroethylene) and 50% pefluoropolyether oil mixture, and about 80% light surfactant;

(c) about 10% High Test Hypochlorite, about 90% of a 30% poly(tetrafluoroethylene) and 70% YR pefluoropolyether oil mixture;

(d) about 10% High Test Hypochlorite, about 50% pefluoropolyether oil; about 20% poly(tetrafluoroethylene), about 10% water, and about 10% Light surfactant;

(e) about 10% High Test Hypochlorite, about 50% pefluoropolyether oil, about 20% poly(tetrafluoroethylene), about 10% Light surfactant, and about 10% water;

(f) about 10% Chloramine T, and about 90% of a 30% poly(tetrafluoroethylene) and 70% YR pefluoropolyether oil mixture;

(g) about 10% Chloramine B, and about 90% of a 30% poly(tetrafluoroethylene) and 70% YR pefluoropolyether oil mixture;

(h) about 10% Iodobenzene diacetate, about 10% light surfactant, and about 80% of a 50% poly (tetrafluoroethylene) and 50% pefluoropolyether oil mixture;

(i) about 8% Iodobenzene diacetate, about 42% pefluoropolyether oil, about 40% poly(tetrafluoroethylene), and about 8% light surfactant;

(j) about 10% Activated Carbon, about 53.8% pefluoropolyether oil, and about 37.5% poly(tetrafluoroethylene);

(k) about 10% XE555 resin, about 40% pefluoropolyether oil, about 30% poly(tetrafluoroethylene), about 10% water, and about 10% light pefluoropolyether oil surfactant;

(l) about 7.5% XE555 resin, about 62.5% pefluoropolyether oil, and about 30% poly(tetrafluoroethylene);

(m) about 5.6% XE555 resin, and about 94.4% pefluoropolyether oil;

(n) about 5% Potassium O,O'-Dioctanylphosphorodithioate, about 49% pefluoropolyether oil, and about 46% poly(tetrafluoroethylene); and (o) about 10% Potassium O,O'-Dibutanylphosphorodithioate, about 45% pefluoropolyether oil, and about 45% poly(tetrafluoroethylene).

14. A topical skin protectant formulation for neutralizing chemical warfare agents into less toxic products comprising:
   (a) a barrier base cream, said barrier base cream comprising about 30–50% poly(tetrafluoroethylene) resins dispersed in about 40–60% perfluorinated polyether oils; and
   (b) about 1–30% of one or more active moieties from the group consisting of: Iodobenzene Diacetate; High Test Hypochlorite; Chloramine T; Chloramine B; active carbon; XE555 resin; and Potassium O,O'-Dibutanylphosphorodithioate; and Potassium O,O'-Dioctanylphosphorodithioate.

15. A topical skin protectant formulation for neutralizing chemical warfare agents into less toxic products comprising one or more active moieties, wherein said one or more active moiety is selected from the group consisting of: Iodobenzene Diacetate; High Test Hypochlorite; Chloramine T; Chloramine B; active carbon; XE555 resin; Potassium O,O'-Dibutanylphosphorodithioate; and Potassium O,O'-Dioctanylphosphorodithioate.

16. The topical skin protectant formulation of claim 15, further comprising a base cream.

17. The topical skin protectant formulation of claim 1, wherein said chemical warfare agents are one or more of the group consisting of blistering agents, G class nerve agents, and VX.

18. The topical skin protectant formulation of claim 17, wherein said blistering agent is sulfur mustard.

19. The topical skin protectant formulation of claim 17, wherein said G class nerve agent is soman.

* * * * *